United States Patent [19]

Chang

[11] Patent Number: 5,503,810
[45] Date of Patent: Apr. 2, 1996

[54] SYSTEM FOR PRODUCING HERBAL CONCENTRATE

[76] Inventor: William Chang, 1015 S. Nogales St., Ste. 120, Rowland Heights, Calif. 91748

[21] Appl. No.: 361,797

[22] Filed: Dec. 20, 1994

Related U.S. Application Data

[63] Continuation-in-part of Ser. No. 71,701, Jun. 4, 1993, abandoned.

[51] Int. Cl.⁶ .............................. F28D 7/00; A61K 35/78
[52] U.S. Cl. ...................................... 422/235; 424/195.1
[58] Field of Search ........................ 422/235; 424/155.1

[56] References Cited

U.S. PATENT DOCUMENTS

| | | | |
|---|---|---|---|
| 4,312,837 | 1/1982 | Papp et al. | 422/224 |
| 4,357,309 | 11/1982 | Arnold et al. | 423/486 |
| 5,334,360 | 8/1994 | Engel et al. | 422/230 |

Primary Examiner—John W. Rollins
Attorney, Agent, or Firm—Seldon & Scillieri

[57] ABSTRACT

A preferred embodiment the present invention provides a system for extracting and concentrating active ingredients from herbs. The herbs are boiled in a suitable extraction medium, such as water or alcohol, in an extraction vessel. The extraction vessel is connected to a vacuum line that both serves to lower the pressure of the extraction vessel and to draw off herbal vapor formed in the boiling process. A vapor condenser cools the herbal vapor, forming an herbal condensate that is collected and periodically reintroduced into the extraction vessel, thereby lowering the density of the herbal liquid. After a predetermined period of time, a first portion of herbal liquid is transferred from the extraction vessel to a concentration tank, while the remainder of the herbal liquid continues to boil in the extraction vessel. In a further preferred embodiment of the present invention, the concentration tank is provided with side and bottom heating elements work together to minimize burning of the contents of the concentration tank.

8 Claims, 5 Drawing Sheets

SYSTEM FOR PRODUCING HERBAL CONCENTRATE

This is a continuation-in-part of application Ser. No. 08/071,701, filed Jun. 4, 1993, now abandoned.

BACKGROUND OF THE INVENTION

1. Technical Field

The present invention relates generally to the field of medicinal herbs, and in particular to systems for extracting and concentrating active ingredients of medicinal herbs.

2. Background Art

In recent years, research in the field of natural drugs has received greater attention world-wide. The World Health Organization and UNESCO have periodically held international conferences on natural drugs. The United States has allocated significant funding for large-scale research on natural products that may be potential sources of anti-cancer drugs. In recent years, Japan has experienced a passion for Chinese herbs.

The international community has attached importance to research in the area of natural drugs for a number of reasons. First, the toxic effects of medications derived from natural products are comparatively few. Further, the human body exhibits comparatively less resistance to natural medications. In addition, sources of natural drugs are relatively abundant, and the time and expense typically required to develop a new drug from natural products is considerably less than that required for developing drugs from non-natural sources.

In the field of natural drug research, particular attention has been devoted to medicinal plants. (As used herein, the terms "herb," "medicinal herb," "plant," and "medicinal plant" are used interchangeably to refer to all herbs and plants, the active ingredients of which can be extracted by boiling in an appropriate medium.) Among all the countries in the world, China is the richest in plant resources, having approximately 35,000 species of higher plants, of which on the order of 5,000 have known medicinal uses. One Chinese text alone, the *Ben Tsau Kang Mu*, lists over 1,892 varieties of such plants, which are widely used and which can play a significant role in the treatment of various disorders. China has a long history of practicing herbal medicine with a wealth of practical experience spanning several thousands of years. The application of modern scientific technology and methods to further organize, research, and advance the practice of traditional Chinese medicine and the use of Chinese herbal remedies is a task of the utmost importance.

It is known in the art that the active ingredients of herbs can be extracted and concentrated. In a typical prior art approach, the herb or herbs to be processed are first boiled in a suitable extraction medium, such as water or alcohol, resulting in an herbal liquid. The herbal liquid is then placed in a concentration tank in which a heat exchanger is used to heat the herbal liquid. The extraction medium evaporates, leaving an herbal paste that can be processed further, as needed.

There are disadvantages inherent in the prior art process. First, it exposes herbs to high temperatures and pressures which can destroy the herbs active ingredients. Further, the concentration vessel and heat exchanger taught by the prior art produce suboptimal yields of herbal concentrate: a certain amount of concentrate is lost due to foaming, a certain amount of concentrate is burned at the bottom and sides of the concentration vessel, and other concentrate becomes trapped in the heat exchanger.

There is thus a need in the art for a high-yield system for extracting and concentrating herbal compounds without exposing them to unduly high temperatures and pressures.

SUMMARY OF THE INVENTION

A preferred embodiment of the present invention provides a system for extracting and concentrating active ingredients from herbs. The herbs are boiled in a suitable extraction medium, such as water or alcohol, in an extraction vessel. The extraction vessel is connected to a vacuum line that both serves to lower the pressure of the extraction vessel and to draw off herbal vapor formed in the boiling process. A vapor condenser cools the herbal vapor, forming an herbal condensate that is collected and periodically reintroduced into the extraction vessel, thereby lowering the density of the herbal liquid. After a predetermined period of time, a first portion of herbal liquid is transferred from the extraction vessel to a concentration tank, while the remainder of the herbal liquid continues to boil in the extraction vessel. In a further preferred embodiment of the present invention, the concentration tank is provided with side and bottom heating elements work together to minimize burning of the contents of the concentration tank.

DESCRIPTION OF SPECIFIC EMBODIMENTS

Figure 1:
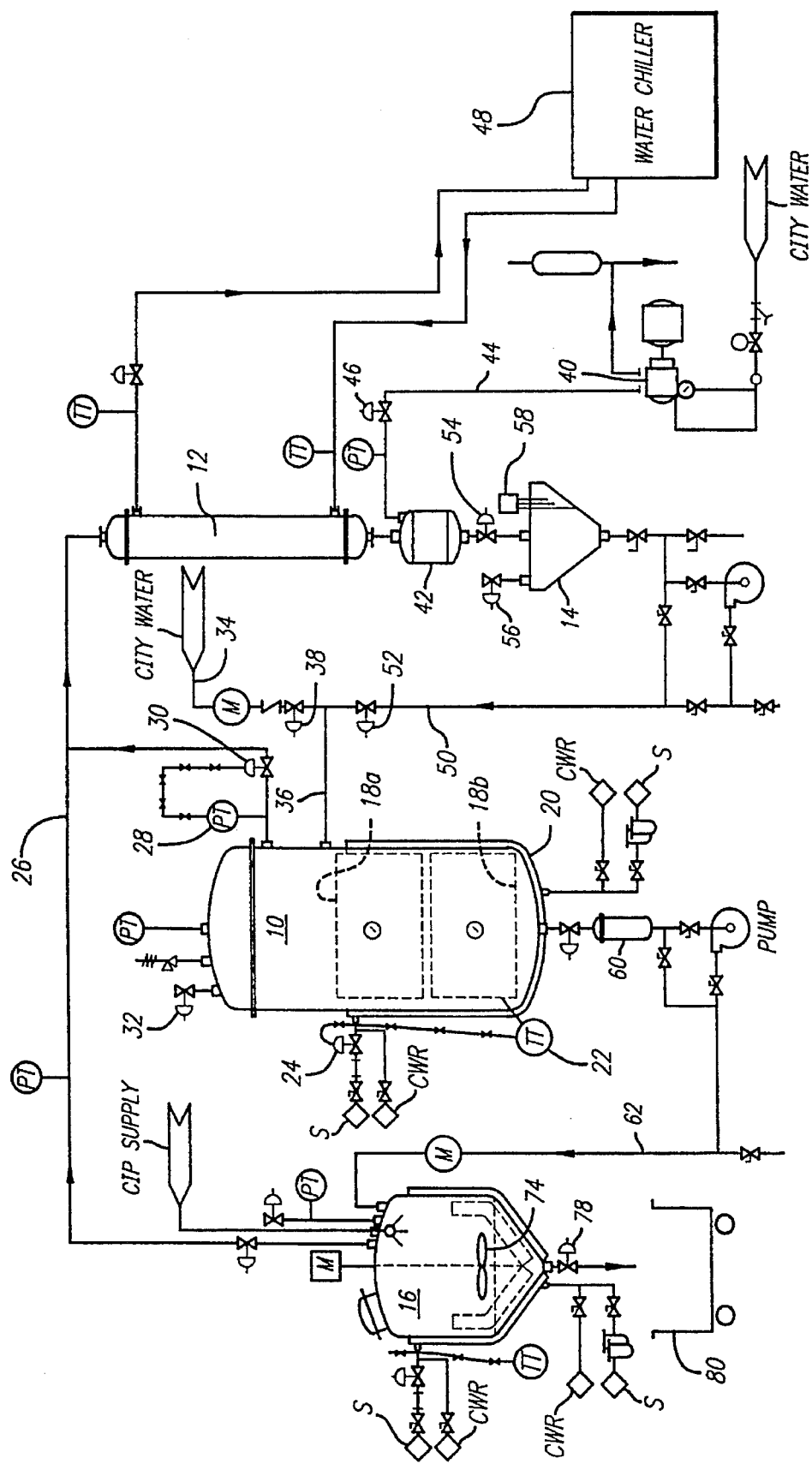
FIG. 1 is a diagram of a preferred embodiment of a system for extracting and concentrating active ingredients from herbs in accordance with the present invention.

FIG. 1 is a diagram of a preferred embodiment of a system for extracting and concentrating active ingredients from herbs in accordance with the present invention. The system comprises an extraction vessel 10, a vapor condenser 12, a condensate collection tank 14, and a concentration tank 16.

A preferred embodiment of the present invention employs a three-phase process for extracting and concentrating herbs. In the first phase, herbs to be processed are placed in the extraction vessel 10 with an appropriate extraction medium, such as water or alcohol. The herbs are then boiled at low pressure to form an herbal liquid. During the boiling process, in a so-called "reflux" action, vapor is drawn from the extraction vessel 10 into the vapor condenser 12, where it is condensed into a clear fluid that is held in the condensate collection tank 14 and then periodically re-introduced back into the extraction vessel 10.

In the second phase, after a predetermined period of boiling, a portion of the herbal liquid in the extraction vessel 10 is transferred to the concentration tank 16. The herbal liquid in the extraction vessel 10 continues to boil, while heat and low pressure are applied to the herbal liquid in the concentration tank 12, causing the extraction medium to evaporate leaving an herbal paste. Like the vapor from the extraction tank 10, vapor from the concentration tank 16 is drawn into the vapor condenser 12, where it is condensed into a clear fluid and periodically reintroduced into the extraction vessel 10.

In the third and final phase, the herbal liquid remaining in the extraction vessel 10 is transferred to the concentration tank 12 for concentration into herbal paste.

In the preferred embodiment shown in FIG. 1, the extraction vessel 10 is a 700-gallon stainless steel vessel with a diameter of 48 inches. The extraction vessel 10 accommodates one or more baskets 18a, 18b containing the herbs that are to be boiled. To handle the baskets 18a, 18b, a half-ton hoist, at least one chain basket, and a 15-foot lift are associated with the extraction vessel, but not illustrated.

The interior of the extraction vessel 10 is heated using means known in the art, such as through the use of heating coils or, as shown in FIG. 1, a steam jacket 20. In the present embodiment, control is provided by a temperature transducer 22, the output of which is fed back to a temperature control valve 24. The pressure of the interior of the extraction vessel 10 is lowered by connecting it to a vacuum line 26, which draws off air from the vessel interior, as well as herbal vapor arising from the boiling of the herbs. Control is provided by a pressure transducer 28, the output of which is fed back to a pressure control valve 30. In addition, a vent valve 32 is provided for connecting the interior of the extraction tank to ambient atmosphere. The temperature and pressure of the interior of the extraction vessel 10 are critical production parameters and are recorded using a Partlow 7000 two-pen chart recorder, not shown.

In the present preferred embodiment, the extraction medium used is tap water, which is introduced into the tank via a water supply line 34 that communicates with the interior of the extraction vessel 10 through a feed line 36. It is suggested that, where appropriate, the tap water be processed by a water softener, such as those manufactured by Culligan. A water feed line valve 38 controls the amount of water introduced into the extraction vessel 10. It will be appreciated by those skilled in the art that alcohol or other suitable extraction media can be used in place of tap water.

The herbs are preferably boiled at a temperature of approximately 67° C. at a pressure of approximately 18" Hg. In this way, the system avoids the use of high temperatures and pressures which could destroy the active ingredients in the medicinal herbs. The medicinally active components the herbs contained in baskets 18a and 18b are extracted into the boiling water, forming an herbal liquid. The boiling herbal liquid produces an herbal vapor containing aromatic and volatile herbal ingredients that is drawn into the vapor condenser 12 through vacuum line 26.

In the present preferred embodiment, the vacuum in line 26 is created by a one-horsepower vacuum pump 40 with a capacity of 80 gallons per minute. The vacuum pump 40 communicates with the vacuum line 26 via the interior of the vapor condenser 12 and an intermediate holding tank 42. The vacuum pump 40 is coupled to the interior of the intermediate holding tank 42 via pump line 44. A valve 46 inserted in the pump line 44 permits selective decoupling of the vacuum pump 40 from the intermediate holding tank 42.

Herbal vapor is drawn into the vapor condenser 12, which is cooled by a Hydromiser water chiller 48 with a capacity of 150,000 BTU/hr. The cooling of the herbal vapor causes it to condense into droplets of herbal condensate. The droplets of herbal condensate are then fed into intermediate holding tank 42, and from there into condensate collection tank 14, which has a capacity of 80 gallons.

The interior of the collection tank 14 is selectively coupled to the interior of the extraction vessel 10 via a return line 50. The return line 50 extends from the output end of the collection tank 14 and shares feed line 36 with the water supply line. A condensate feed line valve 52 permits the feed line 36 to be selectively coupled to the return line 50.

The system control microprocessor is programmed to transfer herbal condensate from the collection tank 14 back to the extraction vessel 10 at predetermined intervals. In the present embodiment, that interval is chosen to be thirty minutes. The transfer is accomplished by: (1) closing a valve 54 between the intermediate holding tank 42 and the collection tank 14; (2) opening a vent valve 56 to raise the pressure in the collection tank 14 to atmospheric pressure; and (3) opening return valve 52 to permit the low pressure in the extraction vessel 10 to draw the condensate into the extraction vessel via return line 50.

In addition, the condensate collection tank 14 is provided with a level probe 58 to sense the rise of condensate level to the top portion of the tank. Upon reaching a predetermined level, the accumulated condensate triggers a microprocessor signal which carries out the valve sequence to transfer condensate back to the extraction vessel 10, thereby preventing overflow if the predetermined level is reached prior to thirty minutes after the last transfer of condensate from the collection tank 14 to the extraction vessel 10.

The periodic feeding back to the extraction vessel 10 of herbal condensate from the collection tank 16 serves to reduce the density of the liquid in the extraction vessel 10 and thereby increase the density differential. This enhances the affinity of the liquid for extracting the active herbal components from the herb or herbs, and thereby aids in the total extraction of the active ingredients from the herbs.

Thus, the low boiling temperature, coupled with the sealed extraction and recirculation of condensate reduces the loss of aromatic and volatile herbal ingredients. The equipment can also be used for high temperature, high pressure extraction where the herbs do not contain aromatic, volatile or other active ingredients which would be destroyed under such conditions. One advantage to the use of high pressure within the extraction vessel is its retardation of foam. In addition, the extraction tank can be used as a high-pressure (e.g., 20 psi) steam sterilizer for raw medicinal herbs, dry herbal tea preparations, herbal liquids, etc.

After approximately two hours of boiling, a portion (preferably half) of the boiling herbal liquid in the extraction vessel is conducted into the concentration tank 16 via a stainless steel filter assembly 60 in flow line 62. Once in the concentration tank 16, the herbal liquid is concentrated by an evaporation process which includes the use of heat and low pressure. Reduction of pressure within the concentration tank accelerates the evaporation/concentration process.

Figure 2B:
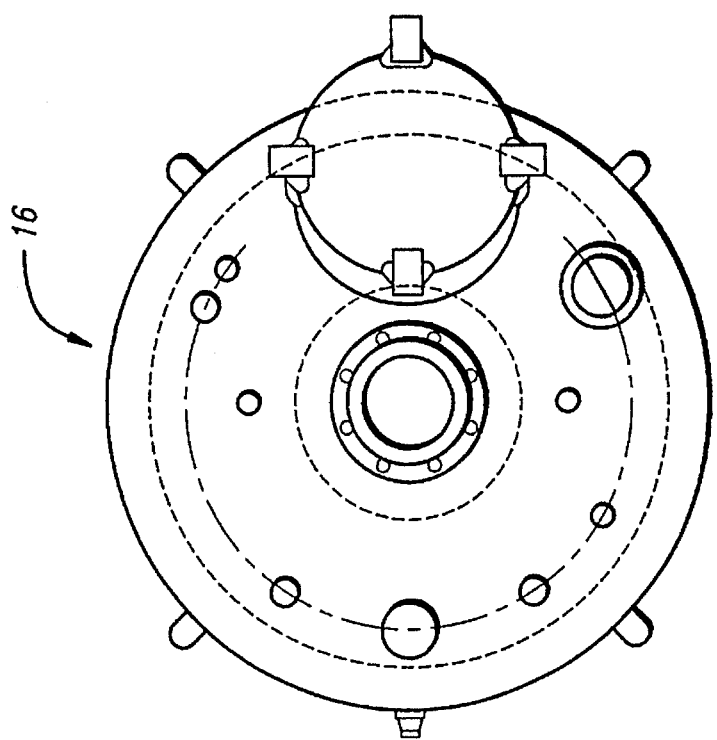
FIG. 2B is a top view of the concentration tank shown in FIG. 2A.
Figure 2A:
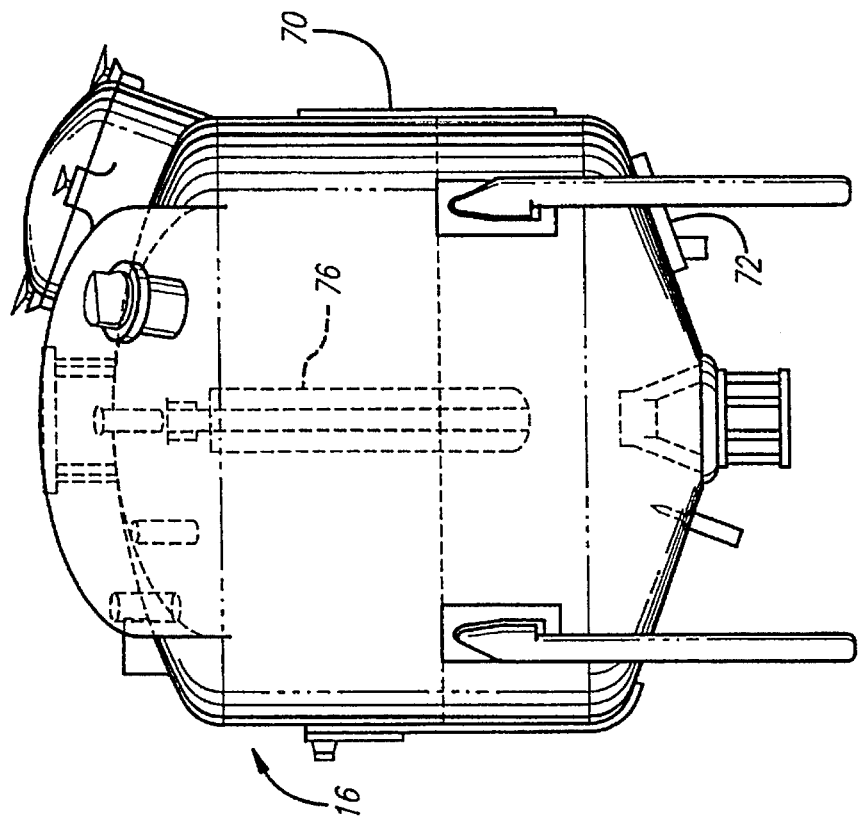
FIG. 2A is a front view of a preferred embodiment of a concentration tank according to the present invention.
Figure 3:
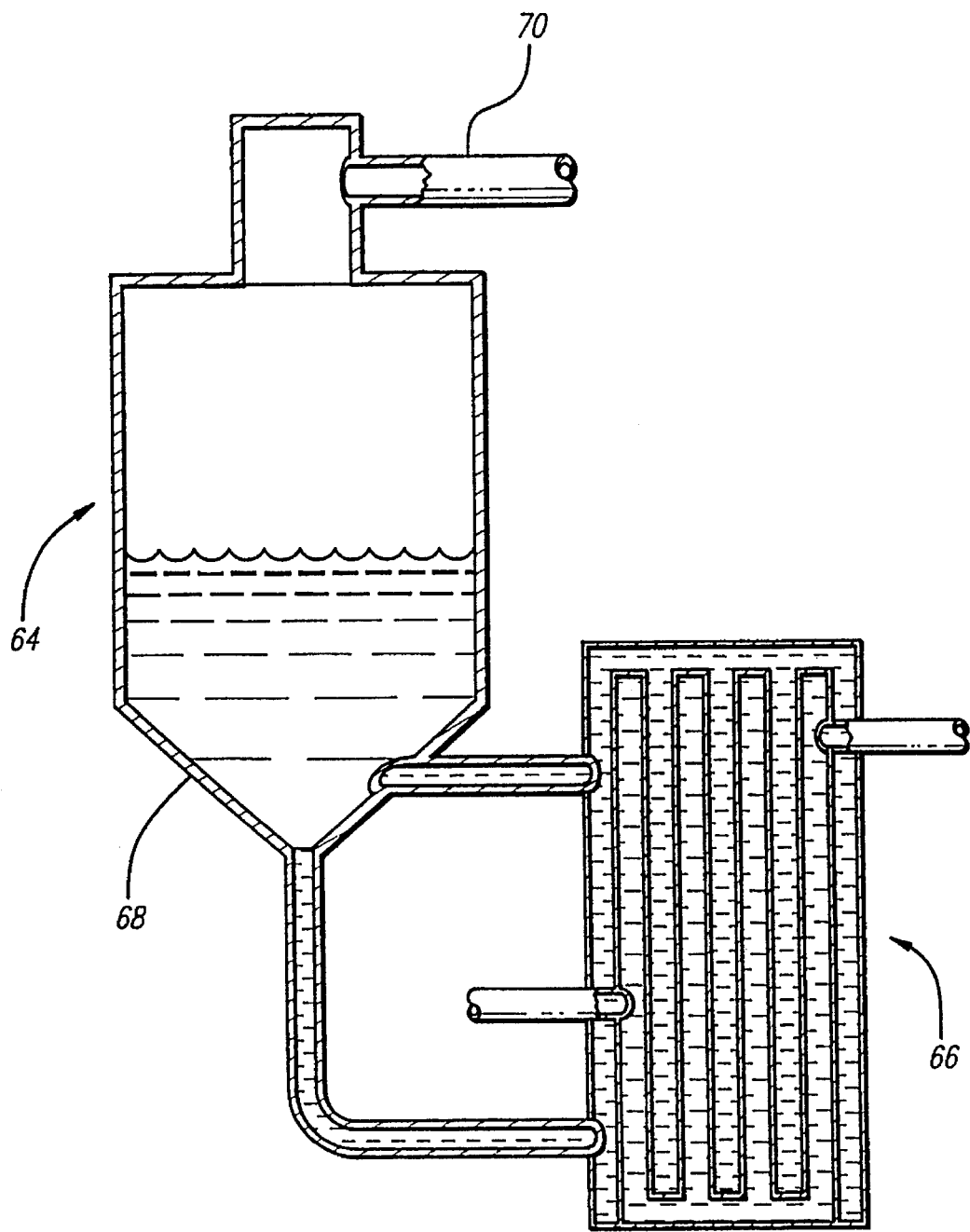
FIG. 3 is a diagram of a concentration tank and heat exchanger according to the prior art.

FIG. 2A shows a front view, and FIG. 2B shows a top view, of the concentration tank 12 shown in FIG. 1. The present concentration tank represents a significant improvement over concentration tanks taught by the prior art. One such prior-art tank 64 is shown in FIG. 3. The prior art concentration tanks are typically used in conjunction with a steam-heated heat exchanger 66. Herbal liquid 68 is drawn from the bottom of the concentration tank 64 into the heat exchanger 66, heated, and then returned at a point higher up in the concentration tank 64. A vacuum line 70 is provided to lower the pressure of the interior of the tank.

The prior-art concentration tank and heat exchanger arrangement shown in FIG. 3 suffers from numerous disadvantages. First, condensed raw material attaches to the walls of the heating tubes inside the heat exchanger, causing both waste of material and cleaning problems. Second, the herbal liquid 68 in the concentration tank 64 evaporates quite slowly due to the small evaporating surface provided by the tank 64. Finally, the interior design of the heat exchanger 66 can result in the formation of foam. The prior-art concentration tank's narrow shape can causes both the foam and herbal vapor to back up through the top outlet into the rest of the system.

The concentration tank 16 provided by the present invention overcomes these disadvantages of the prior art. The shape of the concentration tank 16 shown in FIG. 2 was chosen for the relatively large ratio between its surface area and its height, in order to maximize the rate of evaporation of its contents. In the present preferred embodiment, the concentration tank has a capacity of 375 gallons, and is approximately 48 inches in diameter and 40 inches high. Owing to its relatively large surface area, evaporation occurs rapidly, with rates of up to approximately 30 gallons per hour.

The concentration tank 16 employs a dual steam-jacket heating system to heat the contents in the tank to evaporate liquid therein. A first steam jacket 70 is positioned adjacent the side of the concentration tank 16, and encircles the tank along substantially its entire side wall. The second steam jacket 72 extends along the bottom of the concentration tank 16 to heat only the bottom surface.

When the tank's contents are highly liquid, both the side and bottom steam jackets 70, 72 are on, thereby maximizing evaporation and speeding concentration. Once the contents have been substantially concentrated, the side steam jacket 70 can be turned off, and only the bottom steam jacket 72 operated. This minimizes formation of burnt residue on the tank's side wall, thereby maximizing the yield of herbal concentrate, and also making the tank easier to clean between production runs.

A variable speed, rotating agitator 74, shown in FIG. 1, is provided within the concentration tank 16 to continuously scrape the material along the bottom of the tank, not only preventing residue at the tank's bottom from burning but also enhancing concentration time by bringing fresh material into contact with the heated bottom of the concentration tank. The rotor is driven by a shaft 76, shown in FIG. 2A, which is mounted between the top and bottom of the concentration tank 16. During the processing of the herbal material, the rotation speed of the agitator is gradually increased from an initial speed of approximately 15 rpm to approximately 60 rpm as the tank bottom heats and the quantity of residue increases.

As shown in FIG. 1, the low pressure of the interior of the concentration tank 16 is created by the vacuum line 20, which is driven by vacuum pump 40, as discussed above. Because the extraction tank 10 and the concentration tank 16 are interconnected and use the same vacuum system, extraction and concentration can be conducted simultaneously, resulting in a significant saving of time.

Thus, at this point in the process, the herbal liquid remaining in the extraction vessel 10 continues to boil, with condensed herbal vapor being recirculated back into the extraction vessel. The herbal liquid transferred to the concentration vessel 12 is converted to herbal paste through the evaporation/concentration process described above.

After the herbs have been boiled an additional two hours in the extraction vessel 10, the remaining herbal liquid contained in the extraction vessel 10 is conducted to the concentration tank 16. The extraction process thus ceases, and only the concentration process is carried out. The condensed vapor that has been captured in the collection tank, but not yet fed back to the extraction vessel, is discarded. At this point in the process, it is mostly water.

To improve process efficiency, the extraction vessel, intermediate holding tank, collection tank, and interconnecting lines can be cleaned for the next operation while the remaining concentration takes place. In practice, only five gallons of water are needed to flush these system components. The water used to clean the tank may be recovered and recycled.

Once concentration is completed, the concentrate is removed from the concentration tank 12 by opening a valve 78, shown in FIG. 1, at the tank outlet. The herbal paste is collected in a removable product bin 80 for further processing, as needed. Any residue remaining in the collection tank 16 is then flushed out, and the tank is then cleaned in preparation for the next operation.

Although it has been found in practice that the preferred manner for carrying out the process described above is to transfer one-half of the herbal liquid contained in the extraction vessel to the concentration tank after the herbs have boiled for 2–3 hours, it will be understood that the timing and number of transfers may be varied without departing from the spirit of the invention.

It is also possible to perform a final processing step on the herbal paste taken from the concentration tank and collected in the product bin 80. The paste can be further dried by placing it on the racks within the extraction vessel, which can then operate as a low-pressure vacuum dehydrator/dryer, using the vessel's vacuum process. The vacuum eliminates wetness from the deepest layers of the herbal paste, avoiding incomplete drying, which is commonly encountered when high temperature ovens are used for drying.

Figure 4A:
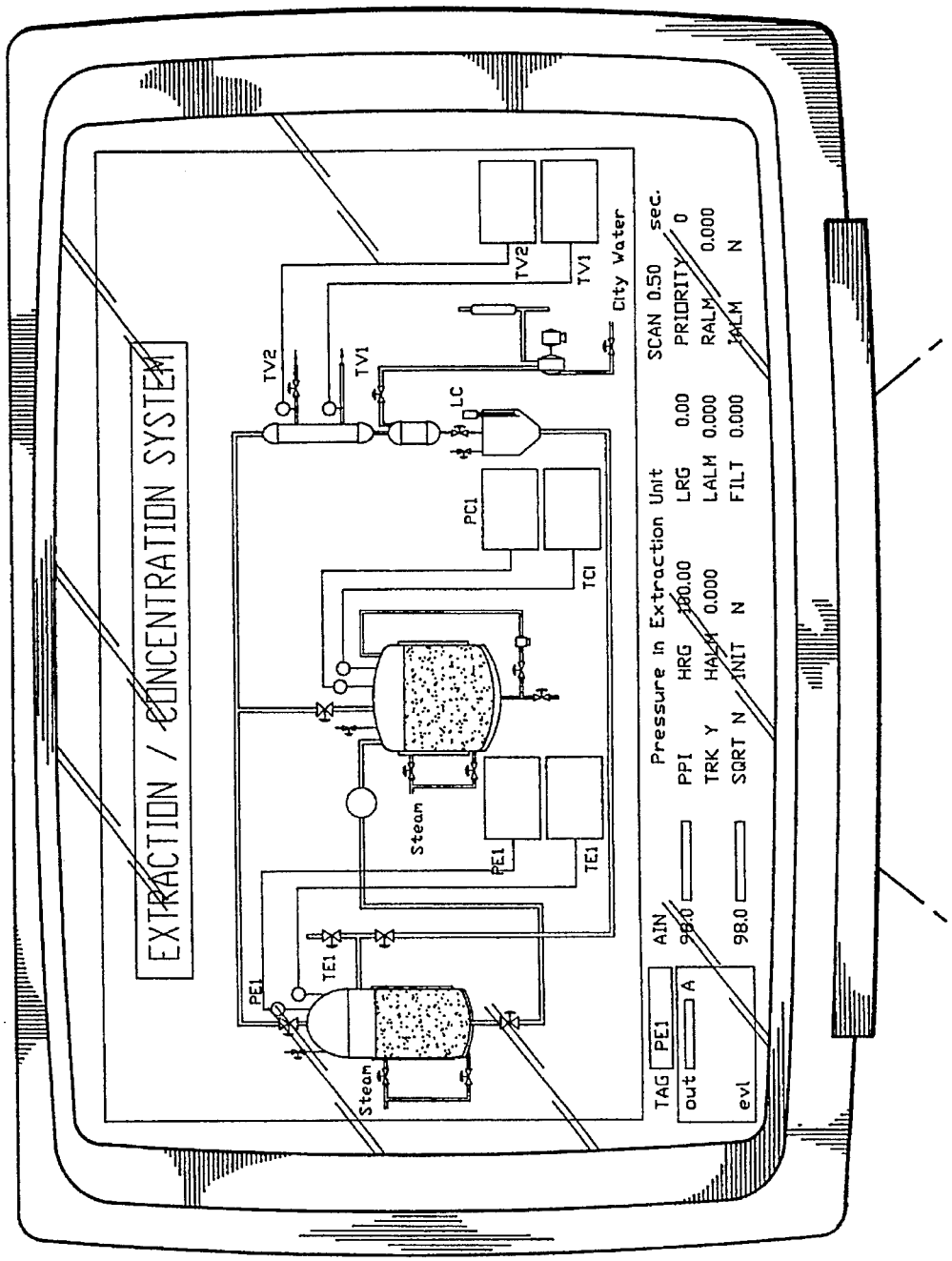
FIGS. 4A and 4B show preferred embodiments of a computer display according to the present invention.
Figure 4B:
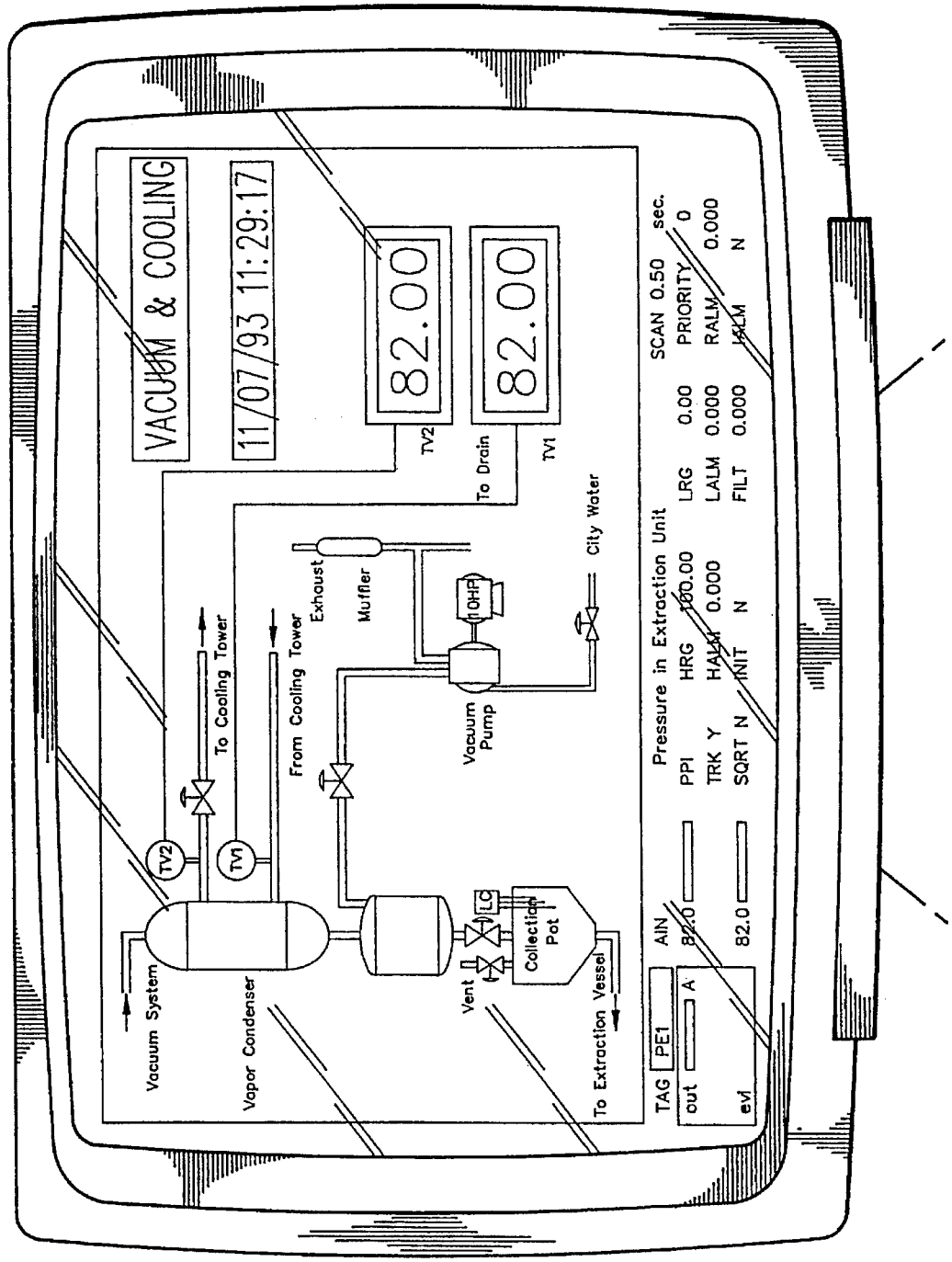

In a preferred embodiment of the present invention, the three-phase described above is controlled by a microprocessor, such as an Allen-Bradley SLC 150. Those skilled in the art will recognize that the microprocessor can utilize sensed temperature, pressure, and timing signals to open and close the various valves described herein at the correct times and in the correct sequence. FIGS. 4A and 4B show a preferred embodiment of the monitor display used with the microprocessor. FIG. 4A provides an overview of the extraction/concentration system. FIG. 4B provides a larger scale view of the vapor condenser, intermediate holding tank, condensate collection tank, and vacuum system.

It will be appreciated by a practitioner of ordinary skill in the art that the present invention can be used to extract and concentrate any herb or medicinal plant that is currently being extracted and concentrated using prior-art methods. The inventor herein has himself successfully used the disclosed system on many herbs, including the following: angelica sinensis, cyperus, Chinese white paeony, moutan, cnidium, licorice, bupleurum, poria cocos, atractylodes, and water plantain.

While the foregoing description includes detail which will enable those skilled in the art to practice the invention, it should be recognized that the description is illustrative in nature and that many modifications and variations will be apparent to those skilled in the art having the benefit of these teachings. It is accordingly intended that the invention herein be defined solely by the claims appended hereto and that the claims be interpreted as broadly as permitted in light of the prior art.

What is claimed is:

1. A system for extracting and concentrating active ingredients from herbs, comprising:

extraction vessel means for boiling herbs in an extraction medium, thereby producing an herbal liquid and an herbal vapor;

vacuum line means connected to the extraction vessel means for drawing air and herbal vapor out of the interior of the extraction vessel, thereby lowering the pressure of the interior of the extraction vessel;

vapor condenser means connected to the vacuum line means for receiving and cooling the herbal vapor, thereby forming herbal condensate;

collection pot means connected to the vapor condenser means for collecting herbal condensate;

means for periodically reintroducing the herbal condensate from the collection pot means into the extraction vessel means, thereby lowering the density of the herbal liquid;

means for drawing off a first portion of herbal liquid from the interior of the extraction vessel while a second portion of herbal liquid remains in the extraction vessel;

concentration vessel means for receiving and concentrating the first portion of herbal liquid, while the second portion of herbal liquid continues to boil in the extraction vessel.

2. A system according to claim 1, wherein the collection pot means further includes:

level detection means for detecting the level of condensate in the collection pot means; and means for transferring condensate from the collection pot means into the extraction vessel means when the condensate has reached a predetermined level.

3. A system according to claim 2, further including:

intermediate holding tank means connected between the vapor condenser means and the collection pot means to hold herbal condensate formed in the vapor condenser means prior to the herbal condensate being transferred to the collection pot means.

4. A system according to claim 3, further including:

vacuum pump means connected to the holding tank means for creating a vacuum in the intermediate holding tank, and thereby in the vapor condenser means and the vacuum line means.

5. A system according to claim 1, wherein the concentration vessel means comprises:

a tank with circular top and bottom faces and a cylindrical side wall, the height of the tank being substantially equal to the diameter of the top and bottom faces;

first heating means disposed along the circumference of the side wall for selectably heating the portion of the interior of the tank adjacent the side wall;

second heating means disposed along the bottom face of the tank for selectably heating the portion of the interior of the tank adjacent the bottom surface;

mixing means mounted to a rotating shaft disposed along the longitudinal axis of the tank for scraping the contents of the tank off of the side wall and bottom surface of the tank.

6. A system according to claim 5, wherein the first heating means comprises a first steam jacket disposed along the cylindrical side wall of the tank and the second heating means comprises a second steam jacket disposed along the circular bottom surface of the tank.

7. A system according to claim 6, wherein the concentration tank means is connected to the vacuum line means, whereby the vacuum line means draws off air and herbal vapor from the interior of the concentration tank, thereby lowering the pressure in the concentration tank means, the herbal vapor being drawn into the vapor condenser means.

8. A system according to claim 7, wherein the bottom surface of the tank includes valved outlet means for removing the contents of the tank, the system further includes a removable collection bin for collecting and removing the contents of the concentration tank means.

* * * * *